United States Patent [19]
Anderson

[11] Patent Number: 5,157,254
[45] Date of Patent: Oct. 20, 1992

[54] REFLECTIVE ELECTRO-LUMINESCENT MEASUREMENT ADAPTER FOR QUALITY CONTROL OF BAKED AND FRIED GOODS

[76] Inventor: John D. Anderson, 1381 Sandalwood Dr., Dunedin, Fla. 34698

[21] Appl. No.: 657,742

[22] Filed: Feb. 19, 1991

[51] Int. Cl.$^5$ ............... G01N 21/84; G01N 21/01
[52] U.S. Cl. .................... 250/239; 73/169; 356/446
[58] Field of Search .......... 73/169; 356/446; 250/239

[56] References Cited

U.S. PATENT DOCUMENTS

| | | | |
|---|---|---|---|
| 1,774,433 | 8/1930 | Gardiner | 99/331 |
| 3,321,636 | 5/1967 | Karrer | 250/574 |
| 3,486,694 | 12/1969 | Henson | 236/15 R |
| 4,484,819 | 11/1984 | Ulrich | 356/446 |
| 5,028,139 | 7/1991 | Kramer et al. | 356/446 |

FOREIGN PATENT DOCUMENTS 3720166 12/1988 Fed. Rep. of Germany ...... 356/446
530724 12/1940 United Kingdom ............... 356/446

Primary Examiner—Constantine Hannaher
Attorney, Agent, or Firm—Silverman, Cass & Singer, Ltd.

[57] ABSTRACT

The present invention relates to a method and a device for measuring vividness by means of the light reflected from the surface of baked and fried goods. The adapter establishes a controlled environment for measuring the light reflected from such surfaces providing and interconnecting a controlled light source, a light sensor, providing a precise angle and precise distances between the light source and the surface and between the surface and the sensor. The measurements obtained by use of the invention define goods which fall within an acceptable range of vividness as it pertains to a consumer preferences.

3 Claims, 8 Drawing Sheets

REFLECTIVE ELECTRO-LUMINESCENT MEASUREMENT ADAPTER FOR QUALITY CONTROL OF BAKED AND FRIED GOODS

FIELD OF THE INVENTION

This invention relates to the indirect measurement of light reflected from a surface to determine vividness or value (i.e., vividness or value refers to lightness or darkness). In particular, the invention relates to an adapter used in the indirect measurement of light reflected from the surface of baked or fried goods in order to define which goods fall within an acceptable range of vividness as it pertains to a consumer's preference for the goods.

BACKGROUND OF THE INVENTION

The appearance of many baked goods such as bread, rolls, muffins and the like, which are sold unfrosted or uncoated, is as important as the taste of the product. Indeed, for many of these items, the appearance of the product sets an image with the user or consumer as to how the product will taste. In a small retail bakery, it is relatively easy for the baker to keep an eye on the product and pull it from the oven at some optimal time when it is properly cooked and its appearance is most attractive. In large commercial bakeries, however, an individual baked good cannot be given such devoted attention. Nonetheless, the purchaser of a commercial bakery's product, often a large retail food store or a mass market restaurant chain, will want assurances that the baked goods they purchase for sale or use are uniform, both within a batch and from day to day, so as to have optimal consumer appeal. Several systems have been described to achieve uniformity in baked goods.

U.S. Pat. No. 1,774,433 to Gardiner describes the regulation of the color of cooked (i.e., baked) products such as bread or cereal by the use of a photoelectric cell interconnected to the oven heating system and U.S. Pat. No. 3,486,694 to Henson describes a system for sensing and controlling the moisture content and/or color of an oven baked product. U.S. Pat. No. 3,321,636 to Karrer describes a photosensitive apparatus for color testing and color control, particularly as it relates to the manufacture of bread flour. While these patents disclose methods of color measurement, all suffer from the defect that the measurements they make are semi-quantitative, lacking definition of output and are strongly affected by light in the surrounding environment. The effect that lighting can have on a person's perception of an item is most easily illustrated by the common experience of purchasing an article of clothing thought to be black or a desired shade of red when viewed in artificial store lighting, only to find in natural light that the article is navy blue or some other shade of red. A similar effect can occur when judging baked or fried goods. The artificial lighting in a commercial bakery can lead a quality assurance person to believe that a given product has the desired vividness whereas when viewed is a different environment, such as a grocery store, restaurant or outdoors, a totally different judgement would be made about the product.

Reflective electro-luminescent measurement (RELM) with a light measuring device as taught by use of the present invention can provide a superior qualitative measurement of baked or fried good. Indeed, these goods can be quantitatively scored or rated relative to selected standards using the present invention. The device of the invention and the procedure for using it vastly improves quality control by the replacing current practices of relying on color photograph comparison, personal interpretation or a combination of both in the scoring of baked goods with a quantitive method of scoring. In so doing, the subjective nature of these older types of evaluation is replaced with an objective standard of measurement that will not only greatly improve a quality assurance program in a bakery, but may also have application in automated oven control and non-bakery applications. The present invention, due to its small size and great portability, can be used to instantly demonstrate a definable product.

SUMMARY OF THE INVENTION

The invention is an adapter or device to be used with a light source and a light meter for measuring the amount of light reflected from the surface of baked and fried goods. The adapter establishes a controlled environment for measuring the light reflected from the surface of goods by providing and interconnecting a controlled light source, a light sensing meter having a light sensor essentially perpendicular to the surface being measured as indicated in the Figures and where the perpendicularity is defined as a line from the light sensor perpendicular to the surface being measured, and providing precise distances from the light source to the surface being measured and from the surface being measured to the light sensor. The adapter further provides a precise angle (A) of reflection between the light source and the light sensor. Incident and reflective light exit and enter the adapter through a common opening. The adapter may be in any size and shape compatible with the good being evaluated. Thus a small, round adapter would be used with some bite-sized cookies or fried meat nugget and a larger, round adapter would be used with, for example, hamburger buns. Similarly, a small oblong or rectangular adapter would be used with hot dog buns or French fries, a larger oblong or rectangular adapter would be used with a common loaf of bread, and a very long, relatively narrow adapter would be used with a loaf of French bread.

DETAILED DESCRIPTION OF THE INVENTION

Figure 1:
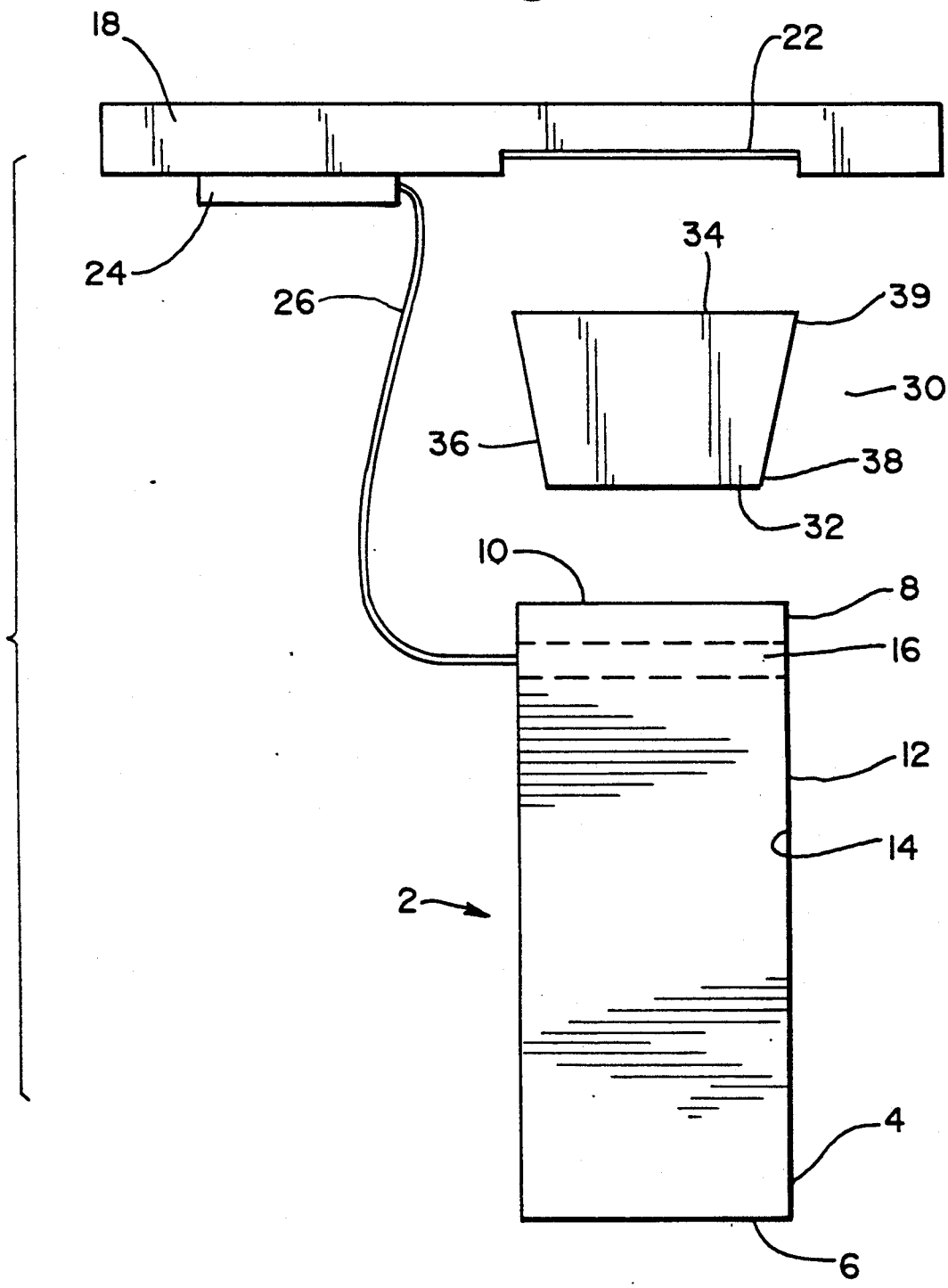
FIG. 1 is a side view of an adapter in which the light source 16 and the light sensor 22 are in an in-line or zero-degree configuration.

This invention related to a new concept, reflective electro-luminescence measurements or RELM, in the baking industry. The measurement of one color, or more accurately, different shades, (lightness or darkness), of that color, constitutes recording variances in vividness or value of the base color. This is precisely the problem confronted in dealing with baked goods. (The terms goods, foods, products and items are used interchangeably herein). Baked goods will range in vividness from ideal through both sides of acceptability and unacceptability. This range is, of course, due to what the end-of-market (EOM) customer will accept more than any other criteria as color is the first decision of any consumer in a buying situation. The biggest problem facing anyone in a quality control and quality assurance program is the problem of being able to objectively evaluate and record the condition of the item under evaluation. In order for an evaluation to be both objective and repeatable, it is necessary to remove as many variables as possible from the evaluation. In evaluating baked goods, such variables encompass the human factor, lighting conditions, viewing distance and viewing angle. The human factor has the greatest impact on the evaluation. Fatigue, lack of concentration, boredom, disposition and attitude all effect the human evaluation; and these factors are magnified by having several people re-evaluating the product at different points along a production line. The end result is that the error margin grows logarithmically along the production line until the product becomes unacceptable. It becomes unacceptable not because, objectively, the product is unacceptable, but because a multiplication of errors has made it so.

The present invention is an adapter which interconnects a light source, a light meter having a light sensor and a food item under evaluation, thereby providing a uniform environment for determining the vividness of the food item. The light source may be any light source such as a light bulb, rectangular lamp, or light ring, either incandescent or fluorescent, which can fit within the internal dimensions of the adapter. The light meter may be a commercial device commonly used in the photographic and the audio/visual industry to measure available light or one made to order according to accepted principles. The adapter of the invention may be mated directly to the meter if the adapter's mounting means is compatible with the meter's, or a flat-cut adapter may be mounted to the meter by a means such as, for example, gluing. Some commercial meters come with an attachment which can be mounted directly to the light meter. The attachment, which has no light source, is often conical or cylindrical in shape and, after attachment to the meter, has one open end. The adapter of the present invention can be joined to this attachment by suitable means such as screw threads, bayonet mount, gluing and the like. If a light meter has no attachment as described above, one may be made and used in accordance with this invention.

In photographic use, a light meter takes ambient light measurements and computes several factors necessary for proper camera adjustment. The resulting light measurement is called the exposure value (EV). By using a proper exposure value, along with other adjustments such as focus, a camera produces a "good" picture. Improper adjustments, especially the exposure value, result in a picture that is either over-exposed (too dark) or under-exposed (too light) relative to an actual object as was seen by the eye at the time the picture was taken. In the baking industry, some combination of oven temperature, baking time, heat dissipation, moisture content, etc., produces a product which is "good" in the eye of the customer. Over-baking produces a product that is too dark and under-baking produces a product that is too light. By using light meter technology and a product judged to be the target or the "standard" (i.e., a replica), the adapter of the present invention permits precise measurement of the vividness of baked goods relative to the standard.

The RELM adapter is designed to be used with light measuring equipment to make quantitative measurements based on the amount of light reflected from the surface of baked or fried goods in order to establish objective, definable and communicable standards regarding the "vividness", lightness or darkness, of the goods. The RELM adapter is an active component which establishes a controlled environment by providing a constant light source at precise angles and distances to and from the good under evaluation in order to facilitate optimum light measurements while eliminating the possibility of outside light contamination. The measurement of the amount of light reflected from the surface of baked or fried goods can be read as voltage, amperage, foot-candles, lux, lumen, exposure value, or even an arbitrary scale. In the preferred embodiments, light reflected from the target standard is set to, for example, a value of zero or one hundred, and the good under evaluation is scored relatively (plus or minus). Measuring area can range from relatively small, about one square inch or less, to relatively large, about one square foot or more, depending on the size of the object being measured and intended purpose of measurement.

The adapter of the present invention may be made of any rigid non-reflective or non-reflective coated material such as, for example, plastic, aluminum, ceramic, steel, etc., and may be molded, machined, fabricated or cast. Preferably the embodiments of the adapter described herein are machined or molded from a black plastic or other machinable/moldable material and have a matte finish. Where non-reflected coatings are used, they may be applied by means such as a paint or may be chemically or electrochemically applied by appropriate techniques.

Referring now to the drawings, FIG. 1 depicts one embodiment of the invention an adapter 2 in which the light source and light sensor are in an in-line or zero degree configuration. The adapter is a hollow body 1 having first end 4 with opening 6, second end 8 with opening 10, outer wall 12, inner wall 14, and light source 16. Light source 16 is located along the interior wall 14 and extends a distance therefrom into hollow body 1. Adapter 2 is used in conjunction with light meter 18 which has light sensor 22 and attachment 30 to measure light reflected from a surface. When in use, light source 16 is powered by the light meter's power supply (not shown) or, preferably by its own power supply 24 to which it is connected by power line 26.

Figure 2:
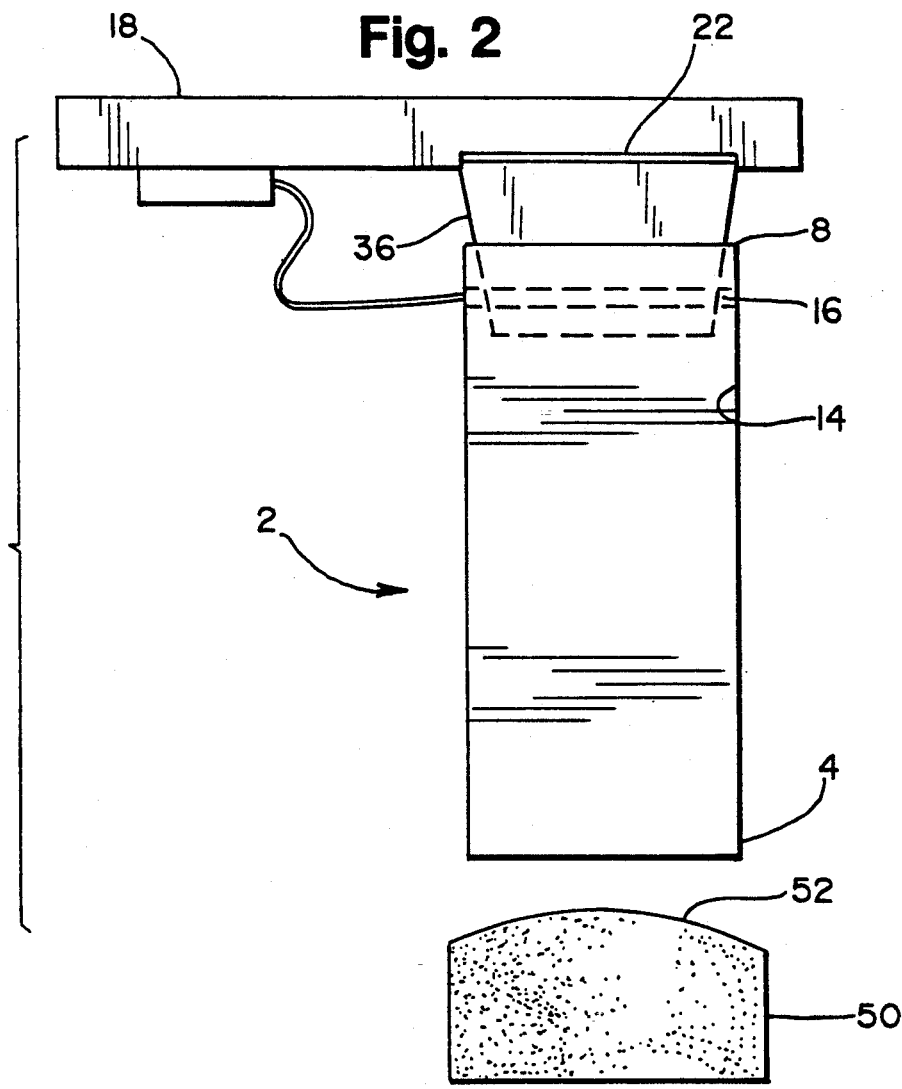
FIG. 2 depicts an adapter of zero-degree configuration assembled to a light meter and positioned over a good whose vividness is to be determined.

Attachment 30 is a hollow body having a first end 38 with opening 32 and a second end 39 with opening 34. When the adapter 2 is used according to the method of the invention, adapter 2, light meter 18 and attachment 30 are joined as shown in FIG. 2. Consequently, attachment 30 second end opening 34 is sized such that the opening and second end 39 circumscribes light sensor 22. Second end 39 is mated to the light meter 18 in a light tight manner by a mount compatible with that on the meter 18 such as, for example, screw threads or bayonet mount, or, if meter 18 has no mounting means, the second 39 may be attached by an appropriate means such as, for example, gluing.

Attachment 30 fits into opening 10 of hollow body 1 such that hollow body 1 second end 8 is joined in a light tight manner to attachment 30 outer wall 36, the joining being at a point between attachment 30 first end 38 and second end 39 such that first end 38 is located closer to hollow body 1 first end 4 than is light source 16; and light source 16 is located between hollow body 1 inner wall 14 and attachment 30 outer wall 36.

FIG. 2 illustrates the assembly of light meter 18, attachment 30 and adapter 2 shown in FIG. 1. FIG. 2 depicts adapter 2 positioned above product 50 which has surface 52. Surface 52 may be flat (not shown) or curved (shown), such curvature being convex (shown) or concave (not shown). When adapter 2 is used to take a reflected light reading, adapter 2 first end 4 is preferably placed in contact with surface 52. Light from source 16 strikes surface 52 whereupon some of the light is reflected back through adapter 2 and attachment 30 to light sensor 22. The light striking sensor 22 is converted into a readable display (not shown) built into the meter.

Figure 3:
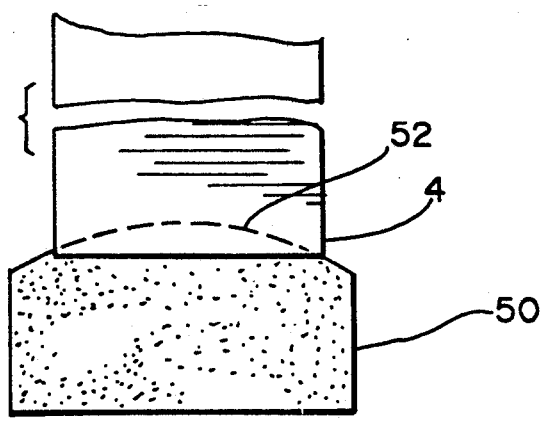
FIG. 3 depicts the contact between the adapter and the good being measured.

FIG. 3 depicts adapter 2 end 4 in contact with surface 52 of a good such as a hamburger or hot dog bun, or a loaf of bread.

Figure 4:
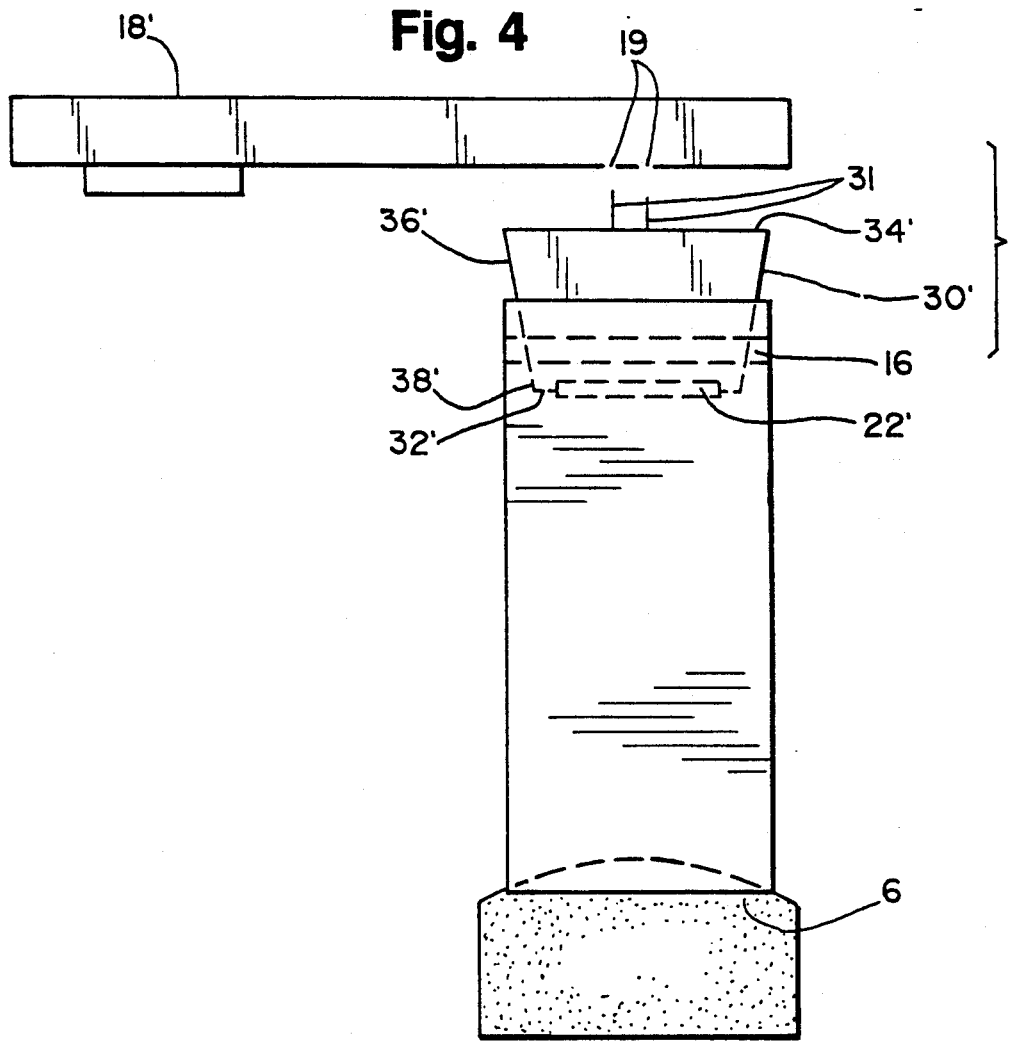
FIG. 4 is a side view of zero-degree configuration in which the light sensor is mounted in a detachable sensor head.

FIG. 4 depicts an alternate in-line or zero degree embodiment of the invention wherein light meter 18' and detachable sensor head attachment 30' are used instead of light meter 18 and attachment 30 described above and shown in FIG. 1. Light meter 18' is a commercial or custom-made meter having one or more receptacles 19 for making electrical contact with sensing head attachment 30'. Sensing head attachment 30' is a hollow body having closed first face 32' with sensor 22' located thereon, closed second face 34' with one or more protrusions 31 for making electrical contact with one or more receptacles 19, and outer wall 36'. Sensor electronic and/or electrical parts may be located within the hollow part of sensing head attachment 30'.

Attachment 30' fits within opening 10 of hollow body 1 such that hollow body 1 second end 8 is joined in a light tight manner to attachment 30' at outer wall 36', the joining being at a point between sensing head attachment 30' first end 38' and attachment 30' second end 39' such that sensing head attachment 30' first face 32', wherein is contained sensor 22', is located a distance from light source and is closer to hollow body 1 first end 4 than light source 16. Sensor 22' located a distance from light source so that light from light source 16 will not directly impinge upon sensor 22'. Light source 16 is located between hollow body 1 inner wall 14 and attachment 30' outer wall 36' and is attached to a p[ower supply as described above in FIG. 1.

Figure 5A:
FIGS. 5a–5c depict various combinations of light source and light sensor shapes.
Figure 5B:
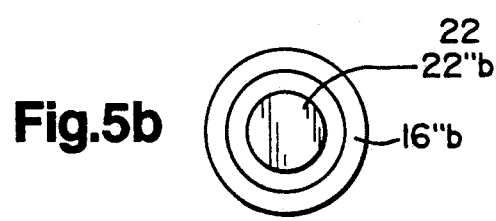
Figure 5C:

FIG. 5a is a view of different shape light sources (16"a-c) and sensors (22"a-c) (hatched areas) used in zero degree embodiments as seen through adapter 2 open face 6. FIG. 5(a) shows a circular light source and square sensor. FIG. 5(b) shows a circular light source and circular sensor. FIG. 5(c) shows an oblong light source and rectangular sensor. Other combinations are possible such as, for example, a rectangular light source and sensor, or an oblong light source and a plurality of interconnected square or circular sensors.

When the adapter of the invention is used, the light meter is calibrated using a set of standards. Generally, one standard will be the "perfect or ideal" item, and the other standards will represent the allowable plus and minus deviations from the ideal standard. If the meter reading of the light reflected from the surface of a good is arbitrarily assigned a value of 100, meter readings greater or less than 100 will represent a surface having greater or less reflectivity, and hence being lighter or darker, respectively, than the ideal good.

The adapter 2, as shown in FIGS. 1-5, preferably has a circular or rectangular interior shape and opening 6. It is within the scope of the invention that the adapter, and particularly opening 6, can have other shapes such as square, oblong or elliptical, star, and the like. The shape of opening 10 can be selected to correspond to the shape of the item.

The length of adapter 2 as shown in FIGS. 1-5 and measured from end 8 to end 4 (or opening 10 to opening 6) is in the range of about 1 inch (2.54 centimeters (cm)) to about 12 inches (30.5 cm). Preferably, the range is from about 2 inches (5.1 cm) to about 6 inches (15.2 cm). The exact length of adapter 2 will such that the combination of adapter 2 and attachment 30 results in a distance between sensor 22 and end 4 which is in the range of about 1 inch (2.54 cm) to about 12 inches (30.5 cm). Preferably the range for the combination is in the range from about 2 inches (5.1 cm) to about 6 inches (15.2 cm). When the opening 6 is circular, the diameter of opening 6 may be any diameter in the range of about 0.1 inch (0.25 cm) (for measuring "pinpoint" areas) to about 20 inches (501 cm) (for measuring large round loaves). The range is preferably in the range of about 0.3 inches (0.76 cm) to about 6 inches (15.2 cm).

The light source 16 and primes thereof as shown in FIGS. 1-5 are preferably circular, rectangular or oblong in shape depending upon the internal shape of the adapter. In rectangular adapter, long tubes along the long walls of the adapter may also be used. The light from light source may be polychromatic, halogen, sodium, tungsten and the like. Polychromatic is preferred.

The adapter of the invention as shown in FIGS. 1-5 may assume various shapes. For example, when measuring loaves of French or Vienna bread, the adapter opening in contact with the bread may be oblong or rectangular. In such instances, the minor axis or dimension of the adapter may be in the range of about 0.1 inch (0.25 cm) to about 6 inches (15.2 cm), and the major axis or dimension may be in the range of about 0.2 inches (5.1 cm) to about 36 inches (91.4 cm). Similarly, a C-shaped adapter may be used to evaluate croissants, a gingerbread-man shaped adapter may be used to evaluate gingerbread men cookies and the like as desired. Other adapter shapes could be used for French fries or fried chicken, pork or beef.

Figure 6:
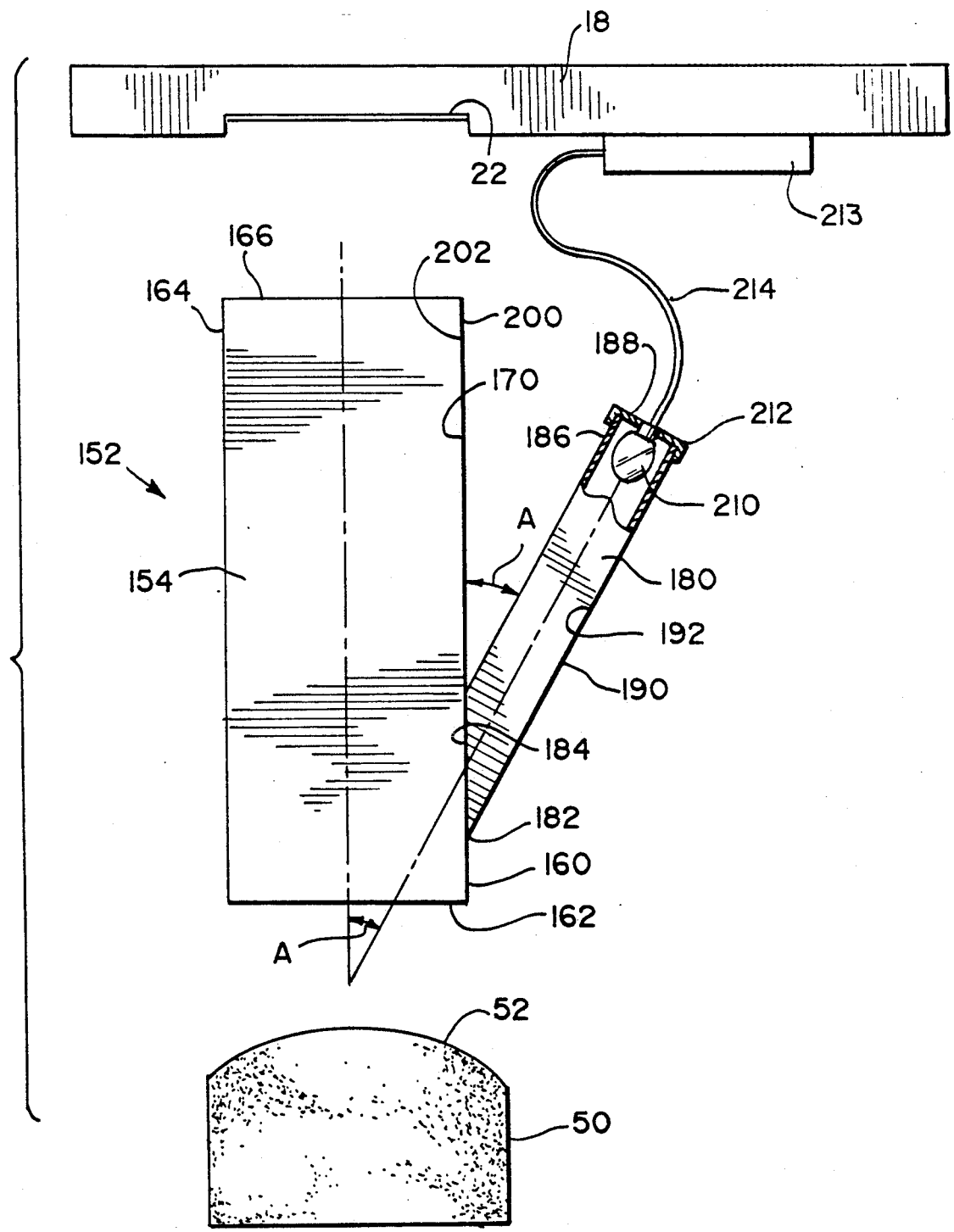
FIG. 6 is a side view of an adapter in which a light source and a light sensor are in an out-of-line or angled configuration defined by angle A.

Refer now to FIG. 6 which depicts an alternate embodiment of the adapter. In this embodiment, the light source and the sensing means sensor are in an out-of-line or angled configuration. That is, a configuration in which there is an angle A between the light source and the light sensor relative to the surface being measured. The adapter 152, as is adapter 2, is made of any rigid, non-reflective or non-reflective coated material such as, for example, plastic, aluminum, steel, etc., and may be molded, machined, fabricated or cast. Preferably the adapter 152 is machined or molded from a black plastic or other machinable or moldable material and has a matte finish. The adapter includes a hollow main body 154 having a first end 160 having opening 162, a second end 164 having opening 166, an outer wall 168 and an inner wall 170, and a hollow side body 180 having a first end 182 having opening 184, a second end 186 having opening 188, an outer wall 190 and an inner wall 192. Main body openings 162 and 166 are through connected and side body openings 184 and 188 are likewise through connected.

Side body 180 angularly extends from main body 154 in a manner such that there is unobstructed interior passage from side body second end 186 past side body first end 182 and into the hollow of main tube 154, thereby creating opening 184 and angle A. The angle A is defined as the angle created by the intersection of (1) an axial line connecting the center point of opening 166 with the center point of opening 162 and (2) an axial line connecting the center point of opening 188 with the center point of opening 184. The size of angle A falls in the range of greater than zero degree to about 75 degrees. Preferably, angle A is in the range of greater than zero degree to about 35 degrees.

Second end 164 of main body 154 is connected to light meter 18 such that the meter's light sensor is completely within opening 166. The connection is made in a light tight manner compatible with the connecting characteristics of the light meter such as, for example, screw treads, a bayonet mount and the like, located at second end 164 either externally at 200 or internally at 202. Alternatively, where the meter manufacturer provides an attachment such as, for example, an extension tube, which can be attached to light meter 14, the adapter can be attached to the free end of the manufacturer's attachment. If permanent attachment is desired, gluing or the like can be used to attach the adapter to the light meter or the manufacturer's attachment.

A light source 210 is located at second end 186 of side body 180 such that the light source 210 extends through opening 188 a distance into the hollow inner part of side tube 180. The light source 210 is seated in cap 212 (or a plug, not shown) which seals opening 188. The light source 210 is connected to a power source 213 by a power connecting line 214 extending from the power supply through cap 212 to either the light source 210 itself or receptacle (not shown) holding the light source. The light source 210 may be any bulb, tube, ring or lamp capable of fitting into the hollow of tube 180. The light source in FIG. 6 is shown as a bulb. The light emitted by light source 210 (like light source 16 previously described) may be polychromatic, laser, halogen, sodium and the like. A polychromatic light source is preferred. The light source 210 (or 16) may be continuous or intermittent. Preferably, the light source is intermittent and is turned or flashed on by the user, using known methods such as by pushing a button switch or built-in electronic control, when the adapter is in use.

The opening 162 of main body 154 may be any shape desired, but for practical reasons the preferred shapes are circular, rectangular, square and oblong, with rectangular and circular being the most preferred. When circular, the diameter of opening 162 may be any diameter in the range of about 0.1 inch (0.25 cm) to about 20 inches (50.8 cm). When rectangular, the major axis of the opening 162 may be in the range of about 0.2 inch (0.51 cm) to about 36 inches (91.4 cm) and the minor axis may be in the range of about 0.1 inch to about 6 inches (15.2 cm).

In the adapter of the present invention, the size and shape of main tube 154 first end opening 162 and second end 164 opening 166 do not have to be identical. The size and shape of second end opening 166 is determined by the size and shape of the mount on light meter 14 or the manufacturer's attachment to which second end 164 is fitted, or by the size and shape of the sensor itself in those cases where the adapter is mounted directly to the light meter such as by gluing. Consequently, the interior wall 170 of main tube 154 may take a variety of shapes. For example, in the easiest to describe case, when openings 162 and 166 are circular, wall 170 will be cylindrical if openings 162 and 166 are the same size and conical if the openings are different sized. More complex combinations of main tube openings are envisioned as being within the scope of this invention. Since light meters generally have round sensors and/or attachment mounts, second end 164 will usually be circular. First end openings, however, can be circular, rectangular, oblong, crescent shaped, star shaped gingerbread man shaped, etc., as previously mentioned.

Figure 7:
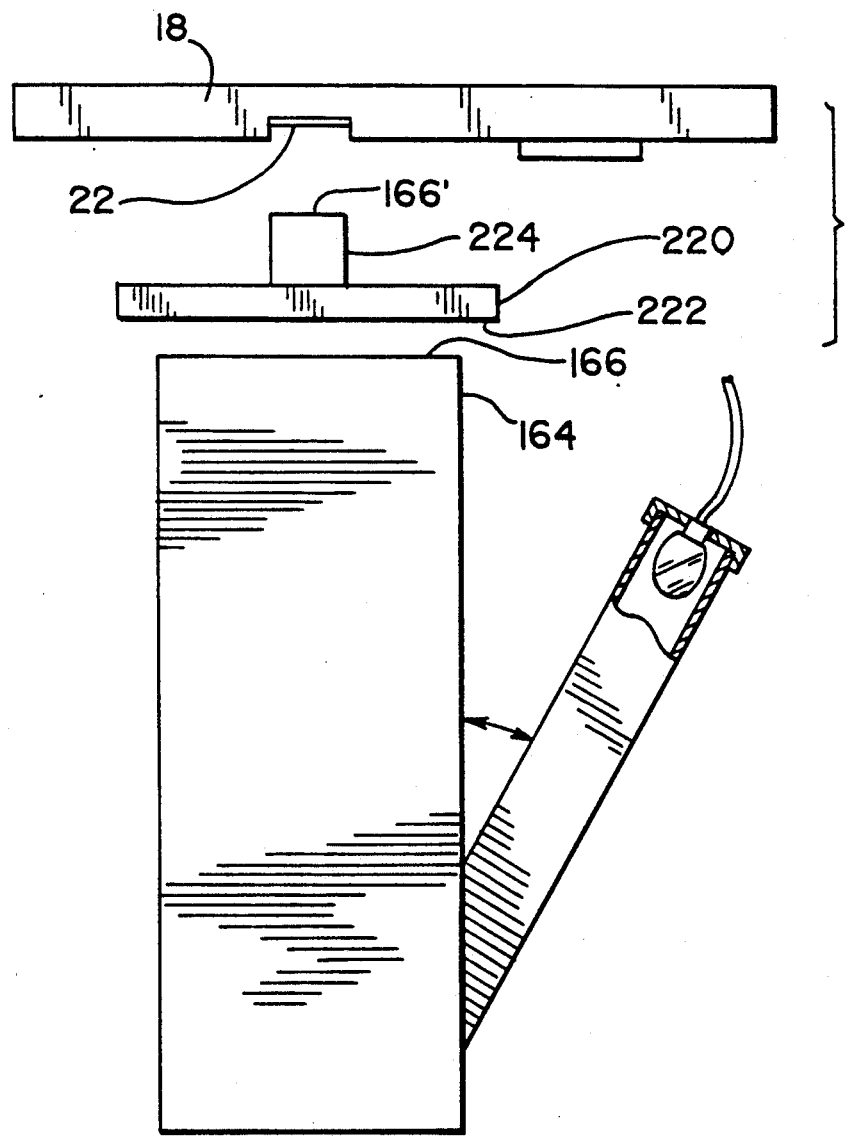
FIG. 7 is the adapter according to FIG. 6 with a reducing cap used to fit the adapter to a light meter.

Alternatively, when second end 164 is of a size and shape which precludes its being attached directly to the light meter or to the manufacturer's attachment, second end 164 is attached to a reducing cap. FIG. 7 depicts, a cap 220 having open end 222, and closed end 226 with hollow protrusion 224 which protrusion defines opening 166′, opening 166′ being mountable of the light meter or attachment. Cap 220 may by externally, internally or facially connected to end 164 by any suitable method.

Figure 8:
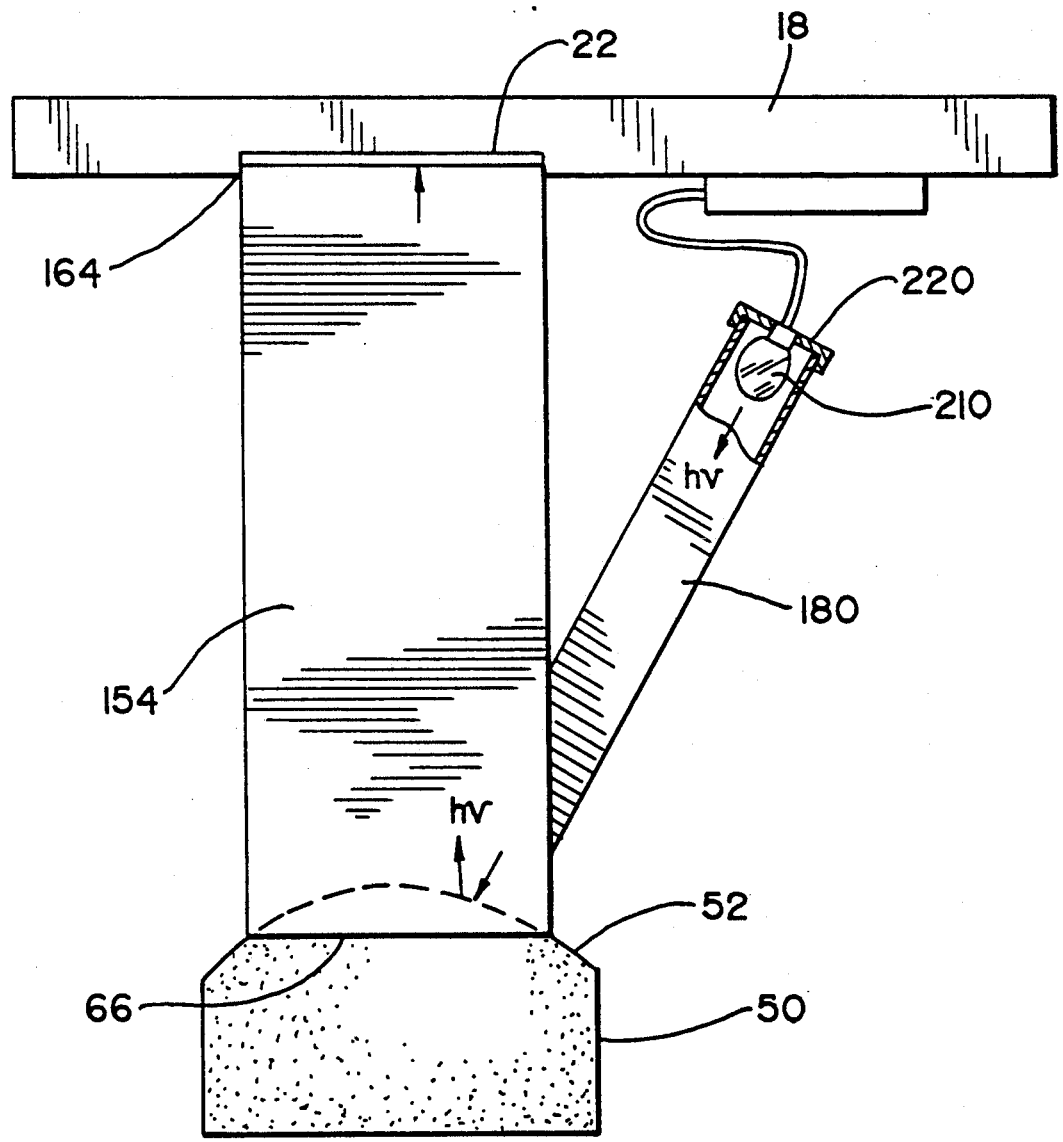
FIG. 8 depicts the adapter of FIG. 6 assembled to a light meter and in contact with a good whose vividness is to be determined.

FIG. 8 depicts the use of the adapter 152 in accordance with the invention. Main body first end 160 is placed in contact with surface 52 of good 50. Light (hv) from light source 210 travels down second tube 180 into first tube 154 and thence to strike surface 52 whereupon a part of the incident light is reflected back up tube 154 from first end 160 to second end 64 and through opening 166, or 166′ when cap 220 (FIG. 6) is used and finally striking light sensor 22 whereupon it is converted into a displayable electrical signal. The distance from light source 210 to opening 162 is in the range of about 1 inch (2.54 cm) to about 6 inches (15.2 cm), and the distance from main tube 154 first end 160 to light sensor 22 is in the range of around 2 inches (5.1 cm) to about 12 inches (30.5 cm). The exact length of main tube 154 will depend on how adapter 152 is mounted to light meter 18. If the main tube 154 second end 164 is mounted directly to the light meter, the length of the main tube 154 will by in the range of about 2 inches (5.1 cm) to about 12 inches (30.5 cm). If either or both of a manufacturer's attachment and cap 220 are used in conjunction with adapter 152, the length of main tube 154 will be reduced by an amount equal to the height of the attachment and/or cap. The resulting distance between the light sensor and opening 162 is in the range of about 1 inch (2.54 cm) to about 12 inches (30.5 cm).

Figure 9:
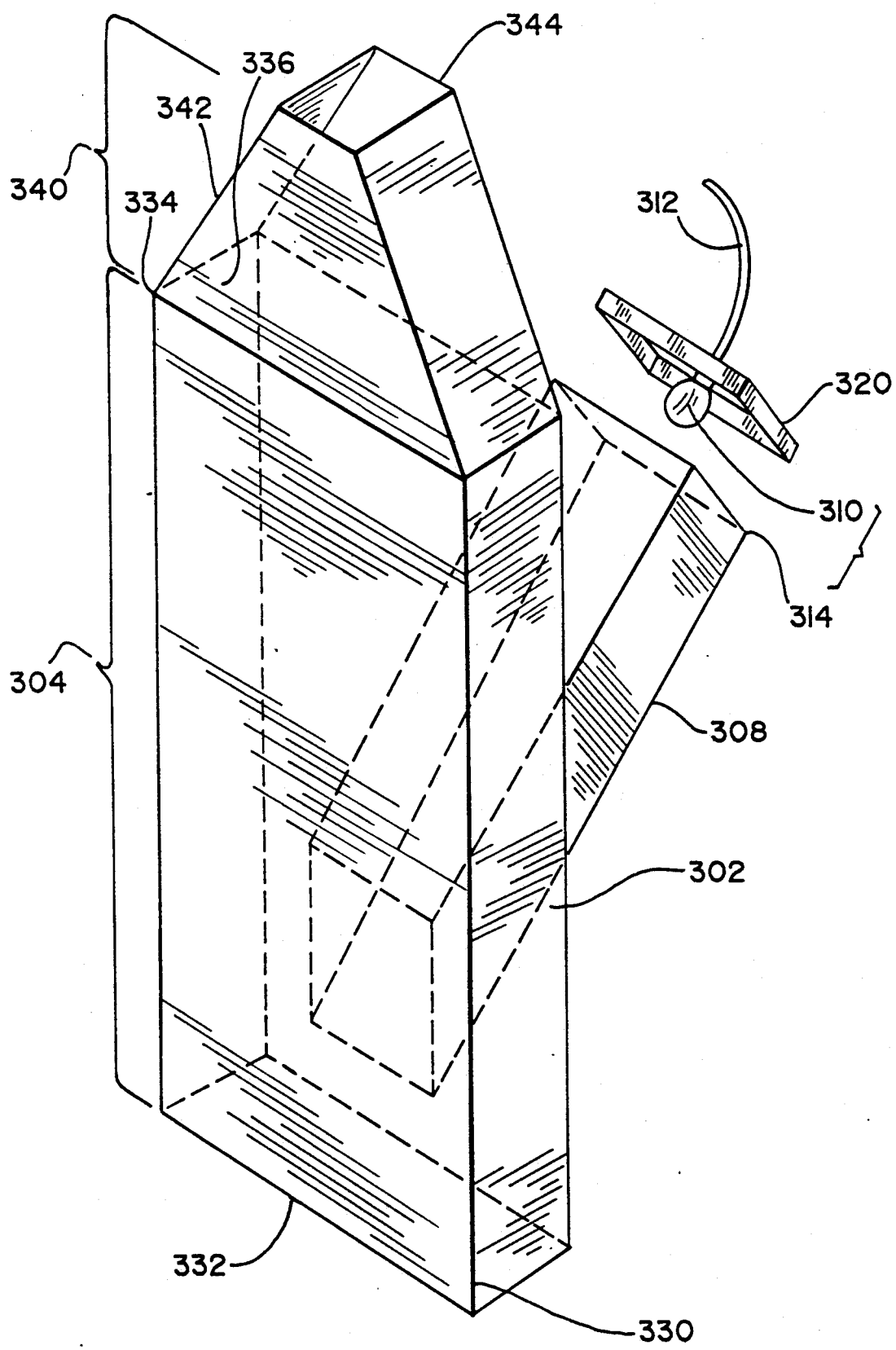
FIG. 9 depicts an adapter for evaluating rectangular or oblong goods in which adapter the light source and light sensor are in an angled configuration.

FIG. 9 depicts a rectangularly shaped adapter 302 according to the present invention. The adapter comprises a rectangularly shaped hollow main body 304 with first cap 340, hollow side body 308 and second cap 320 (or plug, not shown) having light source 310 attached thereto.

Figure 10:
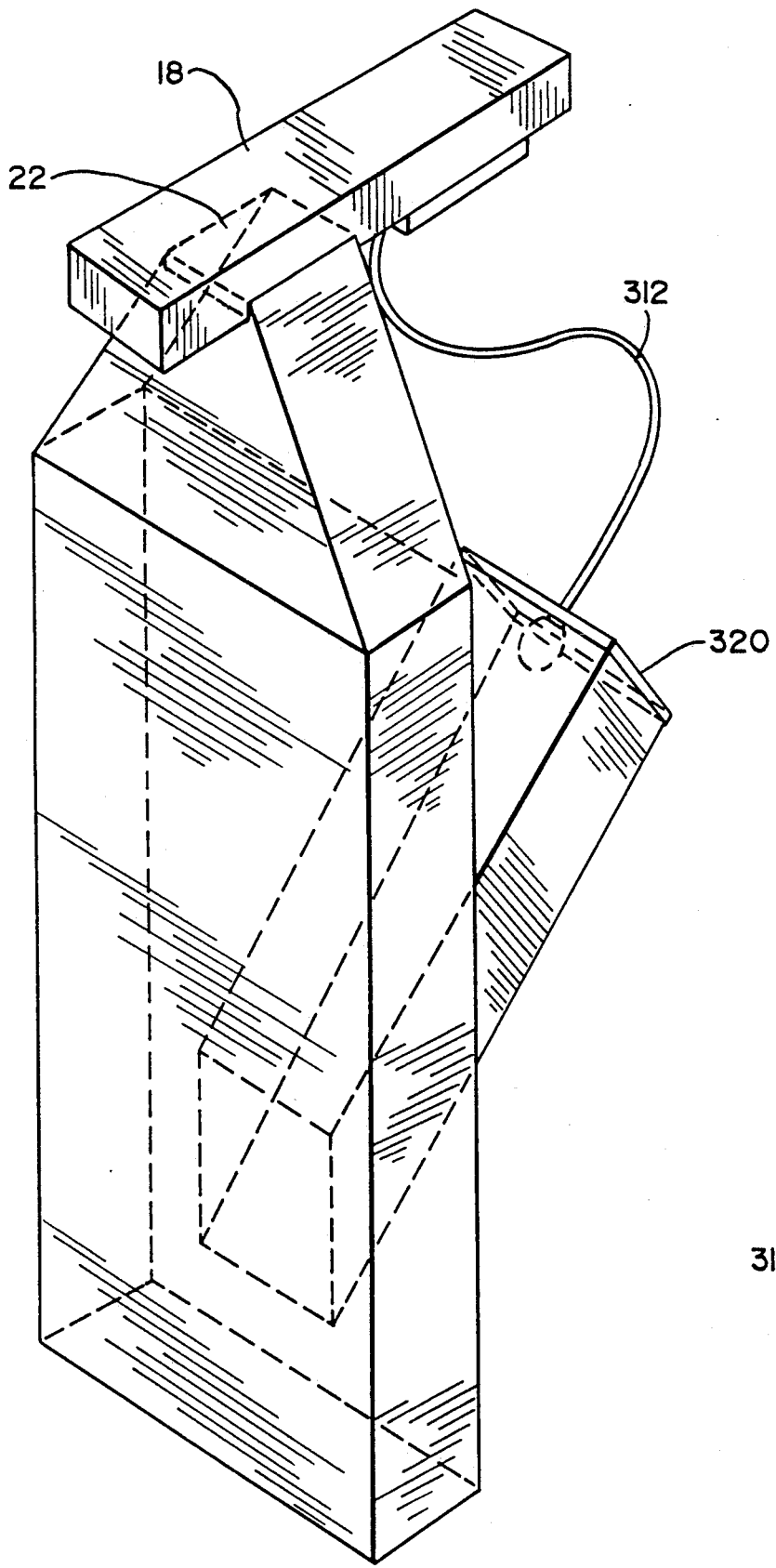
FIG. 10 depicts the adapter of FIG. 9 attached to a light meter.
Figure 11:
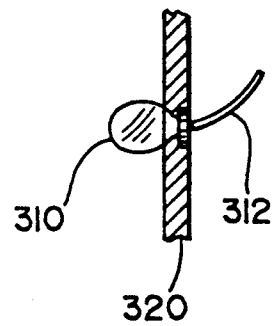
FIG. 11 depicts a light source attached to a side body end cap.

Main body 304 and side body 308 are angularly mounted to define an angle A as described for FIG. 6. Main body 304 has a first end 330 which defines opening 332. When adapter 302 is in use, first end 330 is in contact with the good being evaluated. Main body 304 also has second end 334 which defines opening 336. The adapter 302, as shown in FIG. 9 has a main body cap 340 whose first end 342 has the same dimension as adapter 302 second end 334, and whose second end 344 is of size and shape suitable for attachment to a light meter. Cap 340 first end 342 is removably or permanently joined in a light tight manner to mainbody 304 second end 334. Side body 308 has cap 320 which fits over side body 308 end 314. (Alternatively, a plug or a end mounted cap may be used). Light source 310 is connected to a power source (not shown) by power line 312. FIG. 10 shows the rectangular adapter 302 joined to a light meter. FIG. 11 is a side view of cap 320 (or plug) with light source 310 and power line 312. Power source 310 is illustrated as a bulb in FIGS. 8–10. However, depending on the dimension of hollow body 304, other shapes of light sources, such as tubes, may also be used. In those applications where the main body of adapter 302 is relatively small and where the light meter has a rectangular light sensor, main body cap 340 may not be required and main body second end 334 may be mounted directly to the light meter 18.

The following example demonstrates the use and results obtained using the adapter of the invention. A light meter, bright light and sample baked goods were used in this test. Sample products from two categories, seeded and unseeded hamburger buns, were sorted according to the vividness (contrast) based on comparison with artificial replica buns. It was noted that the replica buns had a slight red tint not characteristic of actual products under normal commercial bakery lighting conditions which are strong in fluorescent and mercury vapor lighting. A real bun, under strong sunlight, will have a slight red hue and closely resemble the replicas. These observations infer that different lighting conditions will provide different results.

Three replica buns were used to set the standards of dark, light and target when measured with a strong control light at a controlled distance using the adapter of the claimed invention. Each bun was measured at the same angle and relative position. The exposure value (EV) of the target bun was used as the base value and was arbitrarily assigned as being 100%. The ratio of EVs of dark/target and light/target, expressed as a percentage, define the range of acceptability on either side of the target bun. (In use, the percentage value, or EV if desired, will be shown on the light meter display). Using this procedure, the acceptability table shown (below) was created and individual buns falling on either side of the light-target-dark range may be rejected. The results were as follows:

| Measured EV | Acceptability Table | | | |
|---|---|---|---|---|
| | Unseeded Bun Target EV = 9.0 | | Seeded Bun Target EV = 9.3 | |
| | Bun | Score % | Bun | Score % |
| 9.7 | real | 92.78 | real | 95.88 |
| 9.6 | real | 93.75 | real | 96.88 |
| 9.5 | real | 94.74 | light | 97.89 |
| 9.4 | real | 95.74 | real | 98.94 |
| 9.3 | light | 96.77 | target | 100.00 |
| 9.2 | real | 97.83 | real | 101.09 |
| 9.1 | real | 98.90 | dark | 102.20 |
| 9.0 | target | 100.00 | real | 103.33 |
| 8.9 | real | 101.12 | real | 104.49 |
| 8.8 | real | 102.27 | real | 105.68 |
| 8.7 | dark | 103.45 | real | 106.90 |
| 8.6 | real | 104.65 | real | 108.14 |
| 8.5 | real | 105.88 | real | 109.41 |

Score = (EV reading ÷ target EV) × 100%
real = actual bun measurement or score calculated for a bun having this EV.

I claim:

1. A device for measuring the amount of light reflected form a surface capable of reflecting light, said device comprising a light source which directly illuminates said surface, a light measuring means having a light sensor adapted to be arranged essentially perpendicular to the surface to be measured, and an adapter angularly interconnecting said source and said means and establishing a controlled environment for measuring the light reflected form the surface by providing a controlled light source for the direct illumination of the surface, (b) the exclusion of extraneous light, (c) a precise distance from said light source to said surface and from said surface to said light measuring means, and (d) a precise angle of reflection of from about 0° to about 35° between said light source, the surface and the light sensor.

2. A device for providing a controlled environment for the measurement of light reflected from a surface by providing a constant light source and a light sensing means having a light sensor at a precise angle to each other, and a precise distance from said light source to said surface and from said surface to said light sensor, said adapter comprising:
 (a) a first hollow body for conducting light between said surface and said light sensor which is essentially perpendicular to said surface;
 (b) a second hollow body for conducting light between a light source contained therein and said surface, said light directly illuminating said surface; and
 (c) said first and second hollow bodies being angularly and interactively connected at an angle greater than zero degrees to about 35°;
 said connection being such that light from the light source passes through said second hollow body, into said first hollow body and to said surface, is reflected from said surface, and said reflected light passes through said first hollow body to said light sensor where the reflected light is converted into a readable signal.

3. A method of measuring the relative vividness of surfaces or the relative vividness of a different points on a single surface, said method comprising:
 measuring the light reflected from a test surface relative to light reflected from a standard surface, said measurement being made in a controlled environment by using an adapter angularly and interactively connecting:
 (a) a light source which directly illuminates said test surface,
 (b) the surface to be measured, and
 (c) a light sensor essentially perpendicular to said test surface; and
 (d) the angle between source, surface and sensor is in the range of about zero degrees to about 35°;
 the controlled environment being such that light from the light source directly illuminates the surface to be measured, is reflected from said surface to said light sensor without contamination by outside light, and whereupon striking said sensor the light is converted into a user readable signal.

* * * * *

UNITED STATES PATENT AND TRADEMARK OFFICE
CERTIFICATE OF CORRECTION

PATENT NO. : 5,157,254
DATED       : October 20, 1992
INVENTOR(S) : John D. Anderson It is certified that error appears in the above-identified patent and that said Letters Patent is hereby corrected as shown below:

Column 4, line 58, after "invention" and after "adapter 2" insert a --comma-- (,) in each instance;

Column 5, line 60, after "source" insert numeral --16--;

line 62, after "source" insert numeral --16--;

Column 8, line 5, after "inch" insert --(0.25cm)--;

line 46, after "used" insert a --comma-- (,);

Column 10, line 21, correct spelling of "form" to --from-- line 21, after "providing" insert --(a)--.

Signed and Sealed this

Fifth Day of October, 1993

*Attest:*

BRUCE LEHMAN

*Attesting Officer*   *Commissioner of Patents and Trademarks*